(12) United States Patent  
Hodorek et al.

(10) Patent No.: US 8,999,000 B2  
(45) Date of Patent: Apr. 7, 2015

(54) ORTHOPEDIC IMPLANT WITH BONE INTERFACE ANCHORING

(75) Inventors: Robert A. Hodorek, Warsaw, IN (US); Antony J. Lozier, Warsaw, IN (US); Cheryl R. Blanchard, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 445 days.

(21) Appl. No.: 12/960,203

(22) Filed: Dec. 3, 2010

(65) Prior Publication Data

US 2011/0224791 A1  Sep. 15, 2011

Related U.S. Application Data

(63) Continuation of application No. 11/344,265, filed on Jan. 31, 2006, now abandoned.

(51) Int. Cl.
*A61F 2/30* (2006.01)
*A61B 17/84* (2006.01)
(Continued)

(52) U.S. Cl.
CPC ........ *A61F 2/30756* (2013.01); *A61B 17/842* (2013.01); *A61B 17/86* (2013.01); *A61B 17/8695* (2013.01); *A61F 2/30749* (2013.01); *A61F 2/30965* (2013.01); *A61F 2/3859* (2013.01); *A61F 2002/2817* (2013.01); *A61F 2002/30004* (2013.01); *A61F 2002/30008* (2013.01); *A61F 2002/30011* (2013.01); *A61F 2002/30075* (2013.01); *A61F 2002/30093* (2013.01); *A61F 2002/30306* (2013.01); *A61F 2002/30462* (2013.01); *A61F 2002/30467* (2013.01); *A61F 2002/30502* (2013.01); *A61F 2002/30616* (2013.01); *A61F 2002/30751* (2013.01); *A61F 2002/30841* (2013.01); *A61F 2002/30957* (2013.01); *A61F 2002/4631* (2013.01); *A61F 2210/0019* (2013.01); *A61F 2210/0061* (2013.01); *A61F 2220/0008* (2013.01); *A61F 2220/0025* (2013.01);
(Continued)

(58) Field of Classification Search
USPC .................................. 623/23.5, 23.54, 23.55
See application file for complete search history.

(56) References Cited

U.S. PATENT DOCUMENTS 4,158,684 A   6/1979   Klawitter et al.
4,502,161 A   3/1985   Wall
(Continued)

FOREIGN PATENT DOCUMENTS

DE   2933174   4/1980
DE   19721661  11/1998
(Continued)

OTHER PUBLICATIONS

"European Application Serial No. 07717480.3, Non Final Office Action mailed Apr. 2, 2008", 1 pg.
(Continued)

*Primary Examiner* — Elizabeth Houston
*Assistant Examiner* — Joshua Levine
(74) *Attorney, Agent, or Firm* — Schwegman Lundberg & Woessner, P.A.

(57) ABSTRACT

A cartilage resurfacing implant is provided for replacing cartilage of an articulating portion of a bone at a skeletal joint having opposed joint surfaces. The cartilage resurfacing implant includes a body having a bearing surface and a bone interface. The bearing surface is able to support articulation with an opposing joint surface.

10 Claims, 2 Drawing Sheets

(51) Int. Cl.
- *A61B 17/86* (2006.01)
- *A61F 2/38* (2006.01)
- *A61F 2/28* (2006.01)
- *A61F 2/46* (2006.01)

(52) U.S. Cl.
CPC  *A61F 2220/0075* (2013.01); *A61F 2220/0083* (2013.01); *A61F 2230/0097* (2013.01); *A61F 2250/0014* (2013.01); *A61F 2250/0017* (2013.01); *A61F 2250/0018* (2013.01); *A61F 2250/0023* (2013.01); *A61F 2250/0057* (2013.01); *A61F 2310/00011* (2013.01)

(56) References Cited

U.S. PATENT DOCUMENTS

| | | |
|---|---|---|
| 4,642,120 A | 2/1987 | Nevo et al. |
| 4,839,215 A | 6/1989 | Starling et al. |
| 4,898,186 A | 2/1990 | Ikada et al. |
| 4,966,924 A | 10/1990 | Hyon et al. |
| 4,996,924 A | 3/1991 | Hyon |
| 5,041,138 A | 8/1991 | Vacanti et al. |
| 5,067,964 A | 11/1991 | Richmond et al. |
| 5,147,904 A | 9/1992 | Jochum et al. |
| 5,282,861 A | 2/1994 | Kaplan |
| 5,314,478 A | 5/1994 | Oka et al. |
| 5,358,525 A | 10/1994 | Fox et al. |
| 5,458,643 A | 10/1995 | Oka et al. |
| 5,556,429 A | 9/1996 | Felt |
| 5,607,474 A | 3/1997 | Athanasiou et al. |
| 5,645,592 A | 7/1997 | Nicolais et al. |
| 5,658,343 A | 8/1997 | Hauselmann et al. |
| 5,702,397 A | 12/1997 | Goble et al. |
| 5,795,353 A | 8/1998 | Felt |
| 5,944,759 A * | 8/1999 | Link ............... 623/18.11 |
| 6,080,194 A | 6/2000 | Pachence et al. |
| 6,132,468 A | 10/2000 | Mansmann |
| 6,140,452 A | 10/2000 | Felt et al. |
| 6,179,840 B1 | 1/2001 | Bowman |
| 6,224,630 B1 | 5/2001 | Bao et al. |
| 6,231,605 B1 | 5/2001 | Ku |
| 6,306,177 B1 | 10/2001 | Felt et al. |
| 6,425,923 B1 | 7/2002 | Stalcup et al. |
| 6,443,988 B2 | 9/2002 | Felt et al. |
| 6,447,514 B1 | 9/2002 | Stalcup et al. |
| 6,494,917 B1 | 12/2002 | McKellop et al. |
| 6,530,956 B1 * | 3/2003 | Mansmann ............... 623/18.11 |
| 6,533,818 B1 | 3/2003 | Weber et al. |
| 6,547,828 B2 | 4/2003 | Scott et al. |
| 6,620,196 B1 | 9/2003 | Trieu |
| 6,629,997 B2 | 10/2003 | Mansmann |
| 6,679,913 B2 | 1/2004 | Homsy |
| 6,719,797 B1 | 4/2004 | Ferree |
| 6,733,533 B1 | 5/2004 | Lozier |
| 6,827,743 B2 | 12/2004 | Eisermann et al. |
| 6,994,730 B2 | 2/2006 | Posner |
| 7,001,431 B2 | 2/2006 | Bao et al. |
| 7,077,865 B2 | 7/2006 | Bao et al. |
| 2001/0033857 A1 | 10/2001 | Vyakarnam et al. |
| 2001/0039455 A1 | 11/2001 | Simon et al. |
| 2002/0022884 A1 | 2/2002 | Mansmann |
| 2002/0029083 A1 | 3/2002 | Zucherman et al. |
| 2002/0077661 A1 * | 6/2002 | Saadat ............... 606/221 |
| 2002/0156531 A1 | 10/2002 | Felt et al. |
| 2002/0173855 A1 | 11/2002 | Mansmann |
| 2002/0183845 A1 | 12/2002 | Mansmann |
| 2002/0183850 A1 | 12/2002 | Felt et al. |
| 2002/0193883 A1 | 12/2002 | Wironen |
| 2003/0008396 A1 | 1/2003 | Ku |
| 2003/0036801 A1 | 2/2003 | Schwartz et al. |
| 2003/0074076 A1 | 4/2003 | Ferree et al. |
| 2003/0078617 A1 | 4/2003 | Schwartz et al. |
| 2003/0195628 A1 | 10/2003 | Bao et al. |
| 2003/0220649 A1 | 11/2003 | Bao et al. |
| 2004/0010312 A1 | 1/2004 | Enayati |
| 2004/0039447 A1 | 2/2004 | Simon et al. |
| 2004/0051213 A1 | 3/2004 | Muratoglu |
| 2004/0133275 A1 * | 7/2004 | Mansmann ............... 623/14.12 |
| 2004/0138754 A1 | 7/2004 | Lang et al. |
| 2004/0153163 A1 | 8/2004 | Posner |
| 2004/0163681 A1 | 8/2004 | Verhaverbeke |
| 2004/0191106 A1 * | 9/2004 | O'Neill et al. ............... 419/2 |
| 2004/0199250 A1 | 10/2004 | Fell |
| 2004/0236424 A1 | 11/2004 | Berez et al. |
| 2005/0043808 A1 | 2/2005 | Felt et al. |
| 2005/0125077 A1 | 6/2005 | Harmon et al. |
| 2005/0171604 A1 | 8/2005 | Michalow |
| 2005/0192674 A1 | 9/2005 | Ferree |
| 2005/0251149 A1 | 11/2005 | Wenz et al. |
| 2005/0251266 A1 | 11/2005 | Maspero et al. |
| 2005/0287187 A1 | 12/2005 | Mansmann |
| 2006/0009853 A1 | 1/2006 | Justin et al. |
| 2006/0079905 A1 | 4/2006 | Beyar et al. |
| 2006/0224244 A1 | 10/2006 | Thomas et al. |
| 2006/0235542 A1 | 10/2006 | Hodorek et al. |
| 2006/0253200 A1 | 11/2006 | Bao et al. |
| 2007/0027230 A1 | 2/2007 | Beyar et al. |
| 2007/0038300 A1 | 2/2007 | Bao et al. |
| 2007/0088444 A1 | 4/2007 | Hodorek et al. |
| 2007/0142916 A1 | 6/2007 | Olson, Jr. et al. |
| 2008/0195205 A1 | 8/2008 | Schwartz |

FOREIGN PATENT DOCUMENTS

| | | |
|---|---|---|
| DE | 20303205 U | 4/2003 |
| DE | 10162205 A1 | 7/2003 |
| DE | 10220368 | 12/2003 |
| EP | 0336861 A1 | 10/1989 |
| EP | 0372811 A1 | 6/1990 |
| EP | 0528080 A1 | 2/1993 |
| FR | 2642301 A1 | 8/1990 |
| GB | 2175506 A | 12/1986 |
| JP | 2001-49018 | 2/2001 |
| JP | 2005-169112 | 6/2005 |
| WO | WO-0130276 A1 | 5/2001 |
| WO | WO 2005/051242 A1 | 6/2005 |
| WO | WO 2006/060555 A1 | 6/2006 |

OTHER PUBLICATIONS

"European Application Serial No. 07717480.3, Office Action mailed Oct. 1, 2008", 1 pg.

Quinton, J.S., et al., "Characterizing the Bonding Mechanisms at Silane-Metal Interfaces: A Model System", Journal of Material Science Letters, vol. 18, pp. 1833-1835, dated Nov. 1999.

PCT International Search Report and Written Opinion for PCT/US2007/061270 dated Feb. 6, 2008.

"Japanese Application Serial. No. 2008-553462, Office Action Mailed Oct. 29, 2012", W/ English Translation, 8 pgs.

"Japanese Application Serial No. 2008-553462, Office Action mailed Nov. 6, 2012", 8 pgs.

"Japanese Application Serial No. 2008-553462, Response filed Jan. 31, 2013 to Office Action mailed Nov. 6, 2012", 10 pgs.

McGraw-Hill Dictionary of Scientific and Technical Terms, Sixth Edition, (2003), 2 pgs.

"U.S. Appl. No. 11/344,265, Advisory Action mailed Oct. 17, 2008", 3 pgs.

"U.S. Appl. No. 11/344,265, Advisory Action mailed Oct. 20, 2010", 3 pgs.

"U.S. Appl. No. 11/344,265, Final Office Action mailed Jan. 15, 2009", 11 pgs.

"U.S. Appl. No. 11/344,265, Final Office Action mailed Jun. 7, 2010", 7 pgs.

"U.S. Appl. No. 11/344,265, Final Office Action mailed Jun. 23, 2008", 10 pgs.

"U.S. Appl. No. 11/344,265, Non Final Office Action mailed Oct. 17, 2007", 14 pgs.

"U.S. Appl. No. 11/344,265, Non Final Office Action mailed Nov. 2, 2009", 7 pgs.

"U.S. Appl. No. 11/344,265, Response filed Mar. 1, 2010 to Non Final Office Action mailed Nov. 2, 2009", 11 pgs.

(56) References Cited

OTHER PUBLICATIONS

"U.S. Appl. No. 11/344,265, Response filed Mar. 19, 2008 to Non Final Office Action mailed Oct. 17, 2007", 11 pgs.

"U.S. Appl. No. 11/344,265, Response filed Jul. 15, 2009 to Final Office Action mailed Jan. 15, 2009", 11 pgs.

"U.S. Appl. No. 11/344,265, Response filed Sep. 24, 2008 to Final Office Action mailed Jun. 23, 2008", 12 pgs.

"U.S. Appl. No. 11/344,265, Response filed Oct. 7, 2010 to Final Office Action mailed Jun. 7, 2010", 11 pgs.

"Canadian Application Serial No. 2,637,888, Office Action mailed Feb. 14, 2013", 2 pgs.

"European Application Serial No. 07717480.3, Office Action mailed Sep. 17, 2008", 2 pgs.

"European Application Serial No. 07717480.3, Office Action mailed Oct. 2, 2008", 1 pg.

"European Application Serial No. 07717480.3, Response filed Oct. 28, 2008 to Office Action mailed Sep. 17, 2008", 3 pgs.

"International Application Serial No. PCT/US2007/061270, International Preliminary Report on Patentability mailed Aug. 5, 2008", 6 pgs.

"Japanese Application Serial No. 2008257154, Response filed Apr. 12, 2012 to Office Action mailed Jan. 17, 2012", 5 pgs.

"Japanese Application Serial No. 2008553462, Office Action mailed Jan. 17, 2012", 6 pgs.

"The American Heritage Dictionary of the English Language", Fourth Edition, Houghton Mifflin Company Boston New York, (2000), 3 pgs.

\* cited by examiner

ORTHOPEDIC IMPLANT WITH BONE INTERFACE ANCHORING

CROSS-REFERENCE TO RELATED APPLICATIONS

This application is a continuation of prior U.S. application Ser. No. 11/344,265, filed Jan. 31, 2006, the entire contents of which is hereby incorporated by reference.

FIELD OF THE INVENTION

The invention relates to implants for skeletal joints. In particular, the invention relates to implants for repairing cartilage defects in the articular surface of skeletal joints.

BACKGROUND

Degenerative and traumatic damage to the articular cartilage of skeletal joints can result in pain and restricted motion. Prosthetic joint replacement surgery is frequently utilized to alleviate the pain and restore joint function. During this surgery, one or more of the articulating surfaces of the joint are replaced with prosthetic bearing components. The replacement components typically include a portion for anchoring the implant adjacent to the joint and a portion for articulating with opposing joint surfaces. For example, during knee replacement surgery, an incision is made into the knee joint to expose the joint. Portions of the articular surfaces of the tibia and femur are removed and artificial joint components are positioned to replace the removed portions. In a total knee replacement, all of the articulating compartments of the joint are replaced with prosthetic components. However, often only one compartment of the knee joint, typically the medial compartment, is impaired. In a unicondylar knee replacement, only the damaged compartment is repaired with prosthetic bearing components. In an even less invasive approach, where the damage is limited to isolated defects in the articular cartilage, it has been proposed to replace just the articular cartilage in the immediate vicinity of the defect.

SUMMARY

The present invention provides a cartilage resurfacing implant for replacing cartilage of an articulating portion of a bone at a skeletal joint having opposed joint surfaces. The cartilage resurfacing implant includes a body having a bearing surface and a bone interface. The bearing surface is able to support articulation with an opposing joint surface.

In one aspect of the invention, the implant includes a flexible body.

In another aspect of the invention, the implant includes a plurality of reinforcing fibers embedded in the body and extending from the bone interface to define a bone attachment.

In another aspect of the invention, the implant includes a plurality of reinforcing fibers embedded in the body and extending from the bone interface to define flexible cables securable to the bone.

In another aspect of the invention, the implant includes a plurality of reinforcing fibers embedded in the body and extending from the bone interface to define slender bristles distributed across the bone interface able to spread the fixation load evenly over the bone interface.

In another aspect of the invention, the implant includes a plurality of reinforcing fibers embedded in the body and extending from the bone interface to define one component of a hook-and-loop fastener arrangement.

In another aspect of the invention, the implant includes a plurality of expandable pegs projecting from the bone interface.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1:
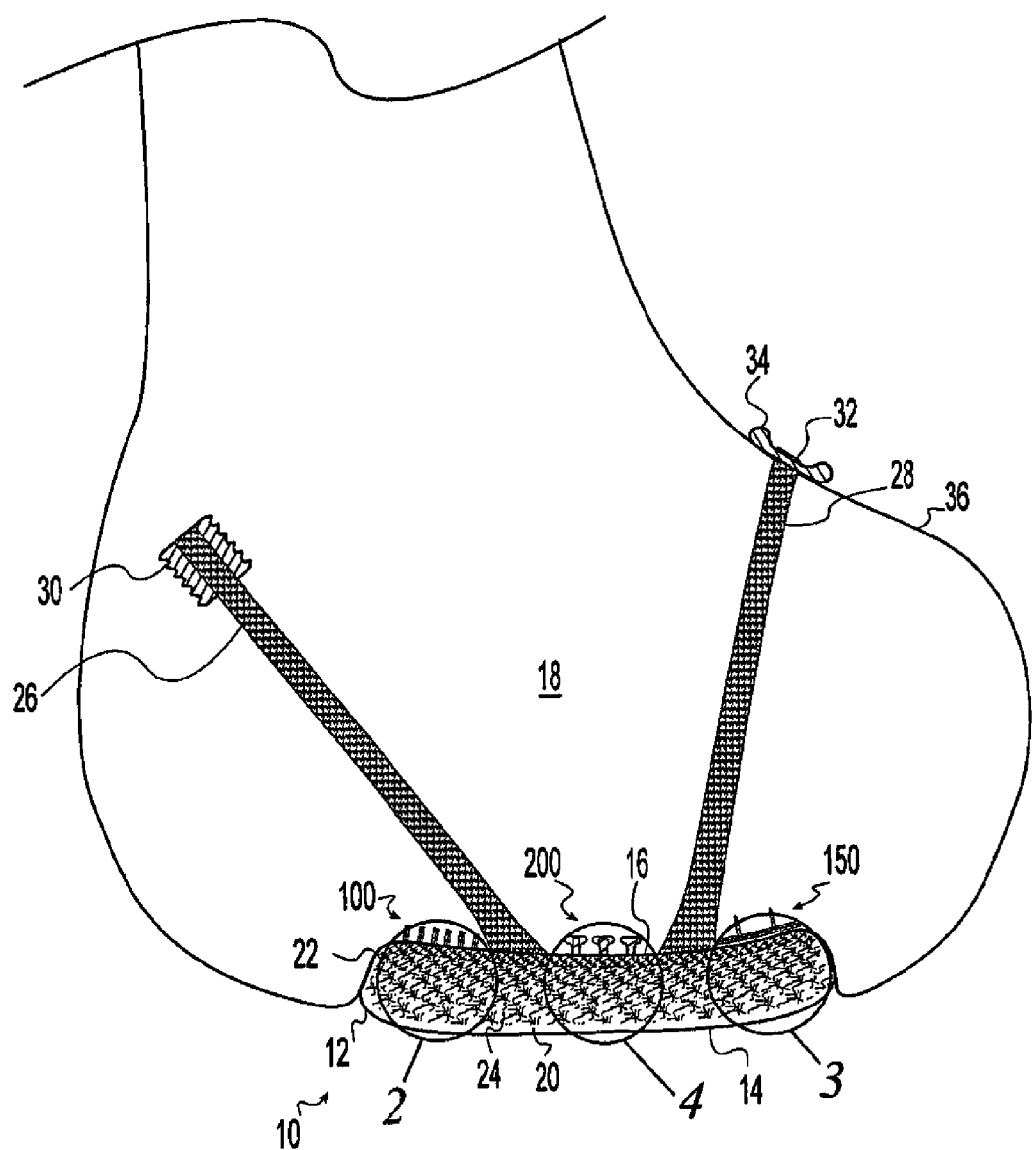
FIG. 1 is a side sectional view of an articulating bone end repaired with an illustrative cartilage resurfacing implant according to the present invention.

Embodiments of a cartilage resurfacing implant include a body having a bearing surface and a bone interface. The implant may function as a replacement for damaged or diseased cartilage of a skeletal joint to sustain continued joint function. The implant may be used to replace a portion of any skeletal joint including, but not limited to, joints of the hip, knee, shoulder, spine, elbow, wrist, ankle, jaw, and digits. The implant may be configured to replace a relatively small defect within the joint, an entire compartment of the joint, or the total joint.

The bearing surface may be made of any material suitable for articulation with natural or prosthetic opposing bearing surfaces. Preferably the bearing material is resilient to facilitate intraoperative flexing, cutting, and/or otherwise shaping of the bearing surface to fit a surgical site. The bearing surface may include polyolefins, polyesters, polyimides, polyamides, polyacrylates, polyketones, and/or other suitable materials. For example the bearing surface may include ultrahigh molecular weight polyethylene. The bearing surface may include a hydrogel having a three dimensional network of polymer chains with water filling the void space between the macromolecules. The hydrogel may include a water soluble polymer that is crosslinked to prevent its dissolution in water. The water content of the hydrogel may range from 20-80%. The high water content of the hydrogel results in a low coefficient of friction for the bearing due to hydrodynamic lubrication. Advantageously, as loads increase on the bearing component, the friction coefficient decreases as water forced from the hydrogel forms a lubricating film. The hydrogel may include natural or synthetic polymers. Examples of natural polymers include polyhyaluronic acid, alginate, polypeptide, collagen, elastin, polylactic acid, polyglycolic acid, chitin, and/or other suitable natural polymers and combinations thereof. Examples of synthetic polymers include polyethylene oxide, polyethylene glycol, polyvinyl alcohol, polyacrylic acid, polyacrylamide, poly(N-vinyl-2-pyrrolidone), polyurethane, polyacrylonitrile, and/or other suitable synthetic polymers and combinations thereof.

The bone interface provides an anchor for the implant. The bone interface may be defined by a unitary body or by a substrate embedded in the body. A substrate may be solid or porous. The bearing surface may attach to the substrate by bonding, mechanical fasteners, porous interdigitation, and/or other suitable attachment methods. For example, the substrate may include an open porous structure in which a portion of the bearing surface is integrated to attach the bearing surface to the substrate. The substrate may be configured to be cemented in place, to be press-fit in place, to receive tissue ingrowth, and/or to be anchored to tissue in any other suitable tissue anchoring configuration. For example, the substrate may include an open porous structure for placement adjacent to body tissue to receive tissue ingrowth to anchor the implant adjacent the tissue. A porous structure may be configured to promote hard and/or soft tissue ingrowth. The porous structures may be in form of an open cell foam, a woven structure, a grid, agglomerated particles, and/or other suitable structures and combinations thereof.

The substrate may include any suitable material including, but not limited to, metals, polymers, ceramics, hydrogels and/or other suitable materials and combinations thereof. For example, a polymer substrate may include resorbable and/or non-resorbable polymers. Examples of resorbable polymers include polylactic acid polymers, polyglycolic acid polymers, and/or other suitable resorbable polymers. Examples of non-resorbable polymers include polyolefins, polyesters, polyimides, polyamides, polyacrylates, polyketones, and/or other suitable non-resorbable polymers. A metal substrate may include titanium, tantalum, stainless steel, and/or other suitable metals and alloys thereof. Preferably the substrate is relatively rigid to provide a suitable surface for hard tissue ingrowth. For example, the substrate may include a porous tantalum material having a structure similar to that of natural trabecular bone. Such a material is described in U.S. Pat. No. 5,282,861 entitled "Open Cell Tantalum Structures For Cancellous Bone Implants And Cell And Tissue Receptors". The material is fabricated by vapor depositing tantalum into a porous matrix. The substrate may include protruding pegs or other bone engaging features to further enhance the connection of the substrate to tissue.

The cartilage resurfacing implant may have a relatively high stiffness near a bone interface to enhance fixation of the implant to the rigid bone surface and a relatively low stiffness near the bearing surface to provide a compliant surface able to move with surrounding natural cartilage tissue. The implant may include a stiffness gradient from relatively high near the bone interface to relatively low near the bearing surface to gradually distribute stresses from the articulating surface to the bone interface and improve its delamination resistance. The cartilage resurfacing implant may include a unitary porous body. The body may include a separate porous substrate joined to the bearing surface. The implant may include a graded porosity that varies from relatively low porosity and high stiffness near the bone interface to relatively high porosity and low stiffness near the bearing surface. For example, a substrate, or a unitary body, may include a porous metal having relatively small pores near the bone interface and relatively large pores toward the bearing surface. Alternatively the substrate, or unitary body, may have uniform or randomly sized pores that vary in the number of pores, or pore density, such that the there is a relatively low pore density and high stiffness near the bone interface and a relatively high pore density and low stiffness toward the bearing surface.

The cartilage resurfacing implant may include a crosslinked polymer structure that has higher crosslinking and stiffness near the bone interface and relatively low crosslinking and stiffness near the articular surface. For example, the implant may include a hydrogel that varies from highly crosslinked to lightly crosslinked to define a stiffness gradient.

The cartilage resurfacing implant may include fibrous reinforcement within the implant body that includes a relatively high percentage of fiber reinforcement near the bone interface to increase the strength and stiffness near the bone and a relatively low percentage of fiber reinforcement near the bearing surface. The fiber reinforcement may have a varying composition from relatively strong fibers near the bone interface to relatively less strong fibers near the articular surface. For example, metal fibers near the bone interface may transition to high strength polymer fibers away from the bone interface to hydrogel fibers at the bearing surface. A unitary porous metal layer may be included for immediate contact with the bone. The reinforcing fibers may project away from the bone interface toward the bone to form fibrous anchors. For example, fibers imbedded in the implant may extend from the back of the implant to form cables for securing the implant to a bone. The cables may be secured in tunnels in the bone or extend to an outer surface of the bone. The cables may be secured with screws, pins, clips, clamps, buttons and/or other fixation members.

In another example, fibers imbedded in the implant may extend from the back of the implant to form slender bristles distributed across the bone interface. For example, the bristles may be distributed to spread the fixation load evenly over the bone interface. This is especially helpful where the implant is flexible to conform to the shape of the bone at the bone interface as it provides many fixation points to stabilize the flexible implant. For example, the bristles may be distributed in any suitable number from 1-100 per square inch of bone interface. Preferably the bristles number 4-20 per square inch. Even more preferably the bristles number 9-16 per square inch. The bristles may have any cross-sectional shape and size but are preferably generally cylindrical and have diameters in the range of 0.010-0.125 inches. More preferably the bristles have diameters in the range of 0.020-0.070 inches and still more preferably the bristles have diameters in the range of 0.030-0.050 inches. The bristles may be pressed directly into the bone to attach the implant to the bone. Alternatively, the bristles may be pressed into predrilled holes. The bristles may have a roughened or projecting surface to enhance their grip on the bone. For example, the bristles may be abrasive grit blasted, plasma sprayed, barbed, and/or otherwise roughened. The bristles may be porous to enhance their grip on the bone by bone ingrowth into pores. For example, the bristles may include porous metals, ceramics, polymers, and/or other suitable porous materials. For example, the bristles may include porous tantalum having a structure similar to natural trabecular bone.

In another example, fibers imbedded in the implant may extend from the back of the implant to form one component of a hook and loop fastener arrangement. For example, the fibers may form hooks and/or loops on the back of the implant. A mating component may be pre-attached to the bone. For example, a mounting base including hooks and/or loops may be installed on the bone and the implant pressed against the mounting base to join the implant to the bone. The mounting base may be attached to the bone with adhesives, screws, staples, and/or other suitable fastening methods. For example, the mounting base may be in the form of a thin, flexible layer of loops attached to the bone with screws and hooks may project from the bone interface of the implant to engage the loops.

In another example, one or more pegs may extend from the back of the implant to engage one or more holes formed in the bone. The pegs may include expandable pegs. For example, expandable pegs may include heat expandable, fluid expandable, and/or otherwise expandable pegs that expand after insertion into the bone. The pegs may expand in width or diameter to grip the bone. The pegs may expand by deploying barbs to grip the bone. For example, partially or fully dehydrated hydrogel pegs may extend from the back of the implant. As the pegs absorb fluid from the surgical site and surrounding tissues, the pegs may expand to fill the holes and grip the bone. As the pegs press against the walls of the holes they form a strong frictional engagement. The pegs may also deform to positively engage the natural porosity of the bone in the walls of the holes. The positive engagement may be further enhanced by forming the holes with a larger diameter inside the bone than at the hole entrance. The hydrogel pegs may expand to at least partially take on the shape of the hole and thus form a positive engagement with the bone. For example, the bone holes may be undercut with a small entry diameter and a larger diameter deeper into the bone. The pegs may deploy barbs upon fluid expansion. In another example, the pegs may include a heat activated expansion mechanism. For example, the pegs may include a shape memory alloy that deploys barbs in the presence of heat from the patient's body. For example, the pegs and/or barbs may be made of shape memory alloy that transforms from a first shape prior to insertion to a second, deployed shape, after exposure to patient body temperature. The pegs may be fiber reinforced to enhance their tensile strength. For example, fibers from the implant may extend into the pegs.

The cables, bristles, hook and loop fasteners, and/or expanding pegs may be formed integrally with the implant or as separate elements subsequently attached to the implant.

The bearing surface may be formed by casting, injection molding, compression molding, machining, and/or other suitable forming processes and combinations thereof. For example, the bearing surface may be compression or injection molded into a porous substrate such that the bearing surface interdigitates with the substrate and is thereby joined to it.

The attachment of the cartilage resurfacing implant to the bone may be enhanced by the use of adhesives including fibrin glue, cyanoacrylate, epoxy, bone cement, and/or other suitable adhesives introduced at the bone interface. The attachment of the cartilage resurfacing implant to the bone may be enhanced by the use of bone growth inducing and/or conducting substances including bone paste, bone chips, bone growth proteins, bone growth peptides, bone marrow aspirate, stem cells, bone attachment proteins, bone attachment peptides, and/or other suitable bone growth promoting substances introduced at the bone interface.

The cartilage resurfacing implant may be provided in a variety of sizes and shapes to facilitate its use in repairing differently sized and shaped cartilage defects. Alternatively, the implant may be provided in a generic form that may be intraoperatively cut to the desired shape and size.

The drawing shows an illustrative cartilage resurfacing implant 10 according to the present invention. The illustrative implant 10 is shown in use to resurface a portion of a femoral articulating surface at a knee joint. However, it is within the scope of the invention for the cartilage resurfacing implant 10 to be configured to replace any amount of any bearing surface in any skeletal joint. The implant 10 includes a body 12 having a bearing surface 14 engageable with an opposing joint surface for joint articulation. The implant 10 includes a bone interface 16 engageable with the bone 18. The illustrative implant 10 includes a fiber reinforced hydrogel structure having a fiber free region 20 adjacent to the bearing surface 14 and a highly fiber reinforced region 22 adjacent to the bone interface 16. The fibers 24 are distributed in a gradient of increasing fiber density from relatively less dense near the bearing surface 14 to relatively more dense near the bone interface 16. The implant 10 is produced by embedding a fibrous preform into the hydrogel during formation of the hydrogel.

The implant 10 forms several attachments to the bone 18. A pair of cables 26, 28 extends from the bone interface 16 into the bone 18 to form localized connections to the bone. The cables 26, 28 preferably are formed from fibers that interdigitate into the implant body 12 and form a portion of the fibrous reinforcement of the body 12. One of the cables 26 is anchored to the bone 18 by a screw 30 threadably engaged with and embedded in the bone. The other cable 28 is anchored to the bone 18 by suspending an eyelet 32 formed in the end of the cable over a button 34 disposed against the cortical surface 36 of the bone 18. The bone interface 16 of the implant 10 includes distributed fixation to more uniformly distribute the dislocation forces over the bone interface 16. The distributed fixation includes a portion including bristles 100 embedded in the bone 18, another portion including a hook and loop fastener 150, and another portion including expanding pegs 200 embedded in the bone. The cables 26, 28, bristles 100, hook and loop fastener 150, and pegs 200 may each be used singly as the only form of fixation for the implant 10 to the bone 18 or in any combination of fasteners.

Figure 2:
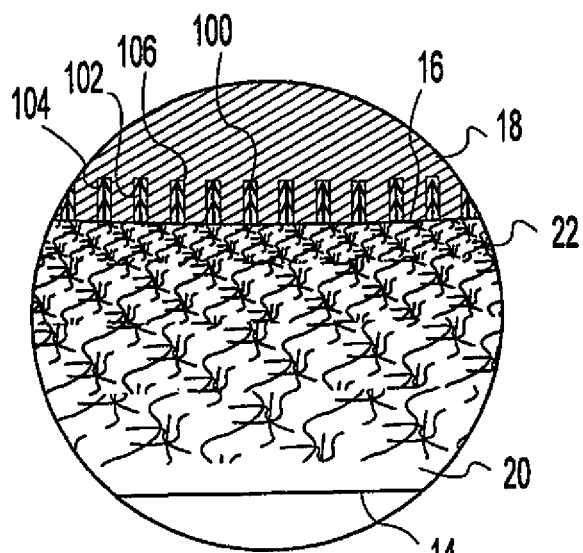
FIG. 2 is a detailed view of the cartilage resurfacing implant of FIG. 1.

The bristles 100 are shown in more detail in FIG. 2. In the illustrative implant 10, the bristles 100 project form the bone interface 16. Each bristle 100 includes a main shaft 102 and barbs 104 extending outwardly from the main shaft 102. The bristles are pressed into holes 106 drilled in the bone 18 and the barbs 104 grip the sides of the holes 106. In the illustrative implant 10, the bristles 100 are extensions of stiff fibers embedded in the implant body 12.

Figure 3:
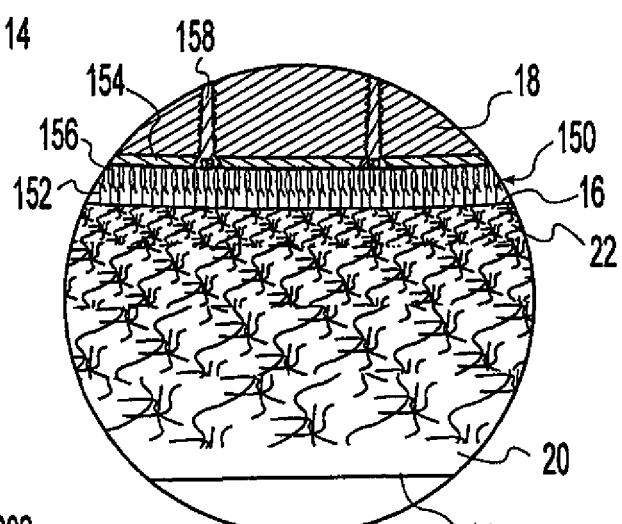
FIG. 3 is a detailed view of the cartilage resurfacing implant of FIG. 1.

The hook and loop fastener 150 is shown in more detail in FIG. 3. In the illustrative implant 10, hooks 152 project from the bone interface 16 and are formed as extensions of stiff fibers embedded in the implant body 12. A mounting base 154 includes loops 156 engageable with the hooks. Bone screws 158 extend through the mounting base 154 and into the bone 18 to secure the mounting base 154 to the bone 18.

Figure 4:
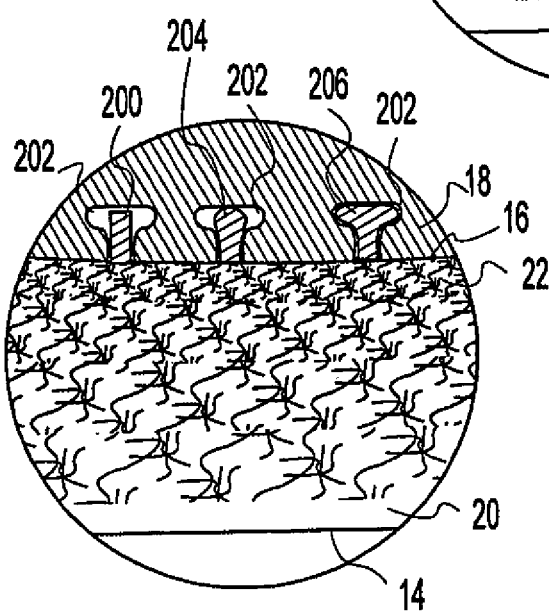
FIG. 4 is a detailed view of the cartilage resurfacing implant of FIG. 1.

The pegs 200 are shown in more detail in FIG. 4. In the illustrative implant 10, each peg 200 is formed as a fiber reinforced extension of the fiber reinforced hydrogel body 12 of the implant 10. The pegs 200 are molded as an integral part of the body 12. The pegs 200 are inserted into holes 202 formed in the bone 18. In the illustrative example, each hole 202 is undercut to have a larger diameter inside the bone 18 than at the surface of the bone 18. As the pegs 200 absorb fluid from the surgical site, the hydrogel swells causing the pegs 200 to fill at least a portion of the hole 202 and lock the implant 10 in place on the bone 18. One of the pegs 204 in FIG. 4 is shown expanded to partly fill a hole 202. This is illustrative of a peg 204 that is in the process of expanding or one that has limited expansion potential due to the nature of its hydrogel composition and/or expansion restraint introduced by fiber reinforcement of the peg 204. Another of the pegs 206 in FIG. 4 is shown fully expanded to fill the undercut hole 202.

In a cartilage resurfacing surgical procedure, a cartilage defect is identified on the articular surface of a bone. The defect may be relatively small and affect only a small area of the articular surface or the defect may be relatively large, or there may be a large number of defects, and affect the entire articular surface. The damaged portion of the articular surface is removed by abrading, cutting, scraping, drilling, and/or any other suitable process. A cartilage resurfacing implant 10 is selected to fit the prepared site. The implant 10 may be provided in a form that is cut or otherwise reformed intraoperatively to fit the prepared site. Fixation holes are formed in the bone, if necessary, and the implant 10 is applied to the prepared site.

Although examples of a cartilage resurfacing implant and its use have been described and illustrated in detail, it is to be understood that the same is intended by way of illustration and example only and is not to be taken by way of limitation. The invention has been illustrated in use to replace a portion of a damaged femoral articular surface at a knee joint. However, the cartilage resurfacing implant may be configured to replace any amount of any articular surface at any skeletal joint. Accordingly, variations in and modifications to the cartilage resurfacing implant and its use will be apparent to those of ordinary skill in the art, and the following claims are intended to cover all such modifications and equivalents.

What is claimed is:

1. An orthopedic implant comprising:
   a flexible body having a bearing surface and a bone interface;
   at least a portion of said bearing surface comprising a polymeric material selected from one or more of a polyolefin, polyester, polyimide, polyacrylate, polyketone;
   said bone interface comprising a porous metal substrate and a plurality of reinforcing porous fibers embedded in the implant, said reinforcing porous fibers adapted for anchoring said implant to a bone of a subject at said bone interface, wherein said reinforcing porous fibers are distributed across the entire bone interface surface to spread the fixation load evenly over the bone interface, wherein said reinforcing porous fibers form bristles distributed across the bone interface and extending freely therefrom, and wherein said bristles are comprised of a porous metal.

2. The implant of claim 1 wherein said bristles are comprised of porous tantalum.

3. The implant of claim 1 wherein said bristles are distributed from 1-100 per square inch across said bone interface.

4. The implant of claim 1 wherein said bristles are generally cylindrical and have diameters in the range of 0.010-0.125 inches.

5. The implant of claim 1 wherein each of said bristles includes a main shaft and at least one barb extending from said shaft.

6. The implant of claim 1 wherein said reinforcing porous fibers extend from said interface and comprise one of a hook or a loop of a hook and loop fastener arrangement.

7. The implant of claim 1 wherein said reinforcing porous fibers comprise differing strengths of fibers that vary from relatively strong fibers near the bone interface to relatively less strong fibers away from said interface.

8. The implant of claim 1 wherein said porous metal substrate comprises an open cell foam.

9. The implant of claim 1 wherein said bearing surface is molded into said porous substrate.

10. The implant of claim 9 wherein said bearing surface is interdigitated with said porous substrate.

* * * * *